United States Patent
Meyer et al.

(10) Patent No.: US 8,947,510 B2
(45) Date of Patent: Feb. 3, 2015

(54) FUNCTIONAL IMAGING OF CELLS WITH OPTICAL PROJECTION TOMOGRAPHY

(75) Inventors: Michael G. Meyer, Phoenix, AZ (US); J. Richard Rahn, Sammamish, WA (US); Anna V. Tourovskaia, Mountlake Terrace, WA (US); Julia Oi Yan Yu, Santa Clara, CA (US); Christy A Lancaster, Seattle, WA (US); Thomas Neumann, Seattle, WA (US); Mark E. Fauver, Seattle, WA (US)

(73) Assignee: Visiongate, Inc., Phoenix, AZ (US)

( * ) Notice: Subject to any disclaimer, the term of this patent is extended or adjusted under 35 U.S.C. 154(b) by 991 days.

(21) Appl. No.: 12/999,515

(22) PCT Filed: Jun. 8, 2009

(86) PCT No.: PCT/US2009/046558
§ 371 (c)(1),
(2), (4) Date: Oct. 14, 2011

(87) PCT Pub. No.: WO2009/155151
PCT Pub. Date: Dec. 23, 2009

(65) Prior Publication Data
US 2012/0105600 A1 May 3, 2012

Related U.S. Application Data

(60) Provisional application No. 61/150,286, filed on Feb. 5, 2009, provisional application No. 61/074,513, filed on Jun. 20, 2008.

(51) Int. Cl.
*H04N 13/02* (2006.01)
*G06T 11/00* (2006.01)
*G01N 15/14* (2006.01)

(52) U.S. Cl.
CPC .......... *G06T 11/006* (2013.01); *G01N 15/1434* (2013.01); *G01N 15/1475* (2013.01); *G01N 2015/1445* (2013.01)
USPC ..................................... 348/50; 348/E13.074

(58) Field of Classification Search
CPC ............. G06T 11/006; G01N 15/1434; G01N 15/1475; G01N 2015/1445
USPC ............................................ 348/50, E13.074
See application file for complete search history.

(56) References Cited

U.S. PATENT DOCUMENTS 8,090,183 B2 * 1/2012 Meyer et al. ................... 382/133
8,155,420 B2 * 4/2012 Meyer et al. ................... 382/131
(Continued)

OTHER PUBLICATIONS

Neuman, Thomas et al., "Simultaneous 3D imaging of Morphology and nanoparticle Distribution in Single Cells with the Cell-CT Technology," Engineering in Medicine and Biology Society, 2008. EMBS 2008. 30th Annual International Conference of the IEEE.
(Continued)

*Primary Examiner* — Christopher S Kelley
*Assistant Examiner* — Asmamaw G Tarko
(74) *Attorney, Agent, or Firm* — George A. Leone; Citadel Patent Law

(57) ABSTRACT

A method for 3D imaging of a biologic object (1) in an optical tomography system where a subcellular structure of a biological object (1) is labeled by introducing at least one nanoparticle-biomarker. The labeled biological object (1) is moved relatively to a microscope objective (62) to present varying angles of view and the labeled biological object (1) is illuminated with radiation having wavelengths between 150 nm and 900 nm. Radiation transmitted through the labeled biological object (1) and the microscope objective (62) within at least one wavelength bands is sensed with a color camera, or with a set of at least four monochrome cameras. A plurality of cross-sectional images of the biological object (1) from the sensed radiation is formed and reconstructed to make a 3D image of the labeled biological object (1).

30 Claims, 14 Drawing Sheets

(56) References Cited

U.S. PATENT DOCUMENTS

| | | | |
|---|---|---|---|
| 8,254,023 B2* | 8/2012 | Watson et al. | 359/432 |
| 2005/0085721 A1* | 4/2005 | Fauver et al. | 600/425 |
| 2006/0023219 A1* | 2/2006 | Meyer et al. | 356/432 |
| 2007/0071357 A1* | 3/2007 | Rahn et al. | 382/275 |
| 2007/0238957 A1* | 10/2007 | Yared | 600/407 |
| 2008/0285827 A1* | 11/2008 | Meyer et al. | 382/131 |

OTHER PUBLICATIONS

Meyer, Michael G. et al., "Automated Cell analysis in 2D and 3D: A comparative study," Pattern Recognition vol. 42 Issue 1, Jan. 2009, Elsevier Science Inc. New York, NY, USA.

True, Lawence D. and Gao, Xiaohu, "Quantum Dots for Molecular Pathology: Their Time Has Arrived," The Journal of Molecular Diagnostics, vol. 9, Issue 1, pp. 7-11, Feb. 2007.

Micro*color: RGB Tunable Filters for High-Resolution Color Imaging, Brochure, Cambridge Research & Instrumentation Inc.

Iiu, Gang L. et al., "Quantized Plasmon Quenching Dips Nanospectroscopy via Plasmon Resonance Energy Transfer," Biomolecular Nanotechnology Center, Berkeley Sensor & Actuator Center, Department of Bioengineering, University of California-Berkeley, Berkeley, CA.

Feridex I.V. (ferumoxides Injectable Solution), May 2007 Bayer Health Pharaceuticles Inc.

* cited by examiner 12A
12B

FUNCTIONAL IMAGING OF CELLS WITH OPTICAL PROJECTION TOMOGRAPHY

RELATED APPLICATIONS

This application hereby claims the benefit of prior filed U.S. provisional patent application No. 61/074,513, filed Jun. 20, 2008, of Rahn et al., entitled "Functional Imaging of Cells with Optical Projection Tomography," which is incorporated herein by this reference, and also hereby claims the benefit of prior filed U.S. provisional patent application No. 61/150,286, filed Feb. 5, 2009, of Rahn et al., entitled "Method for Applying Mass Conservation to Fluorescent Optical Tomography," which is also incorporated herein by this reference.

TECHNICAL FIELD

The present invention relates to optical tomography microscopy imaging systems in general, and, more particularly, to optical projection tomography for functional microscopy, in which a small object, such as a biological cell, is labeled and illuminated with optical radiation for imaging and reconstruction into a 3D image.

BACKGROUND

Advances in imaging biological cells using optical tomography have been developed by Nelson as disclosed, for example, in U.S. Pat. No. 6,522,775, issued Feb. 18, 2003, and entitled "Apparatus and Method for Imaging Small Objects in a Flow Stream Using Optical Tomography," the full disclosure of which is incorporated by reference. Further developments in the field are taught in Fauver et al., U.S. patent application Ser. No. 10/716,744, filed Nov. 18, 2003 and published as US Publication No. US-2004-0076319-A1 on Apr. 22, 2004, entitled "Method And Apparatus Of Shadowgram Formation For Optical Tomography," and Fauver et al., U.S. patent application Ser. No. 11/532,648, filed Sep. 18, 2006, having a related application published on Mar. 27, 2008 as PCT Publication WO2008/036533, entitled "Focal Plane Tracking For Optical Microtomography," the full disclosures of which are also incorporated by reference.

In the field of optical tomography continuous scanning from multiple perspectives is used to acquire projection images from, effectively, an infinite number of adjacent focal planes. In one example, the focal plane of an optical imaging system is mechanically translated along an axis perpendicular to the focal plane through the thickness of a specimen during a single detector exposure. This is often referred to as "scanning" the focal plane. The process is repeated from multiple perspectives, either in series using a single illumination/detection subsystem, or in parallel using several illumination/detection subsystems. In this way, a set of pseudo-projections is generated, which can be input to a 3D tomographic image reconstruction algorithm. The method disclosed may be useful in applications such as high resolution optical tomography of small objects.

Specimen preparation for optical tomography typically begins when patient specimens are received from a hospital or clinic. The specimens are processed to remove non-diagnostic elements, while retaining objects of interest, such as biological cells. Except in the case of live cells, specimens are fixed and then stained. Live cells may be stained, but are usually not fixed. Stained specimens are then mixed with an optical gel or fluid, inserted into a micro-capillary tube and images of objects, such as cells, in the specimen are produced using an optical tomography system. The resultant images comprise a set of extended depth of field images from differing perspectives called "pseudo-projection images." The set of pseudo-projection images can be reconstructed using backprojection and filtering techniques to yield a 3-D reconstruction of a cell of interest.

The 3-D reconstruction then remains available for analysis, enabling the quantification and the determination of the location of structures, molecules or molecular probes of interest. An object such as a biological cell may be labeled with at least one stain or tagged molecular probe, and the measured amount and location of this probe may yield important information about the disease state of the cell, including, but not limited to, various cancers such as lung cancer, breast cancer, prostate cancer, cervical cancer and ovarian cancer.

Functional imaging of cells may be carried out using fluorescent optical projection tomography microscopy (FOPTM). Unfortunately, a common problem in fluorescence microscopy is photobleaching, in which some of the fluorophores permanently cease to emit light. This can occur over time periods ranging from seconds to minutes, and results in a reduction of the signal level, with a concomitant decrease on the signal-to-noise ratio.

Another problem that can occur during FOPTM is poor focus. Poor focus typically results from a focal-plane scan range that does not encompass the entire object thickness. This focusing error yields an image with lower contrast between dark and light regions than would otherwise be obtained.

Yet another problem may be introduced by the presence of a gradient in the light intensity across the field of view. A typical cause of this phenomenon is misalignment of the optical components in the camera system.

In the absence of these problems, the total light emission detected by an FOPTM camera is expected to stay the same for each of the pseudo-projections in a data set, since each pseudo-projection samples the entire volume and therefore all the fluorophores. There is an unmet need in the art to provide increasing amounts of accurate, detailed information about the cell structure at the functional and molecular level. This need is exacerbated by the fact that fluorescence presents a problem for conventional tomography, since fluorescence is typically produced by a light source within the reconstruction volume, along the projection path.

The present disclosure provides new and novel solutions to overcome problems due to photobleaching and other errors that may be present in an optical tomography microscopy system.

BRIEF SUMMARY OF THE DISCLOSURE

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A method for 3D imaging of a biologic object in an optical tomography system is provided. The method includes:

(a) labeling the subcellular structure of a biological object by introducing at least one nanoparticle-biomarker;

(b) positioning the labeled biological object relatively to a microscope objective to present varying angles of view;

(c) illuminating the labeled biological object with radiation having wavelengths between 150 nm and 900 nm so that the at least one nanoparticle-biomarker is selected to emit or absorb radiation having wavelengths between 150 and 900 nm;

(d) filtering a portion of the produced radiation using a set of filters to produce filtered signals within a set of wavelength bands;

(e) sensing the filtered signals transmitted through the labeled biological object and the microscope objective within the set of wavelength bands to produce image data;

(f) repeating steps (b) through (e) until a set of image data from varying angles of view has been produced;

(g) forming a plurality of cross-sectional images of the biological object from the set of image data; and (h) reconstructing the plurality of cross-sectional images to form a 3D image of the labeled biological object.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

Figure 1:
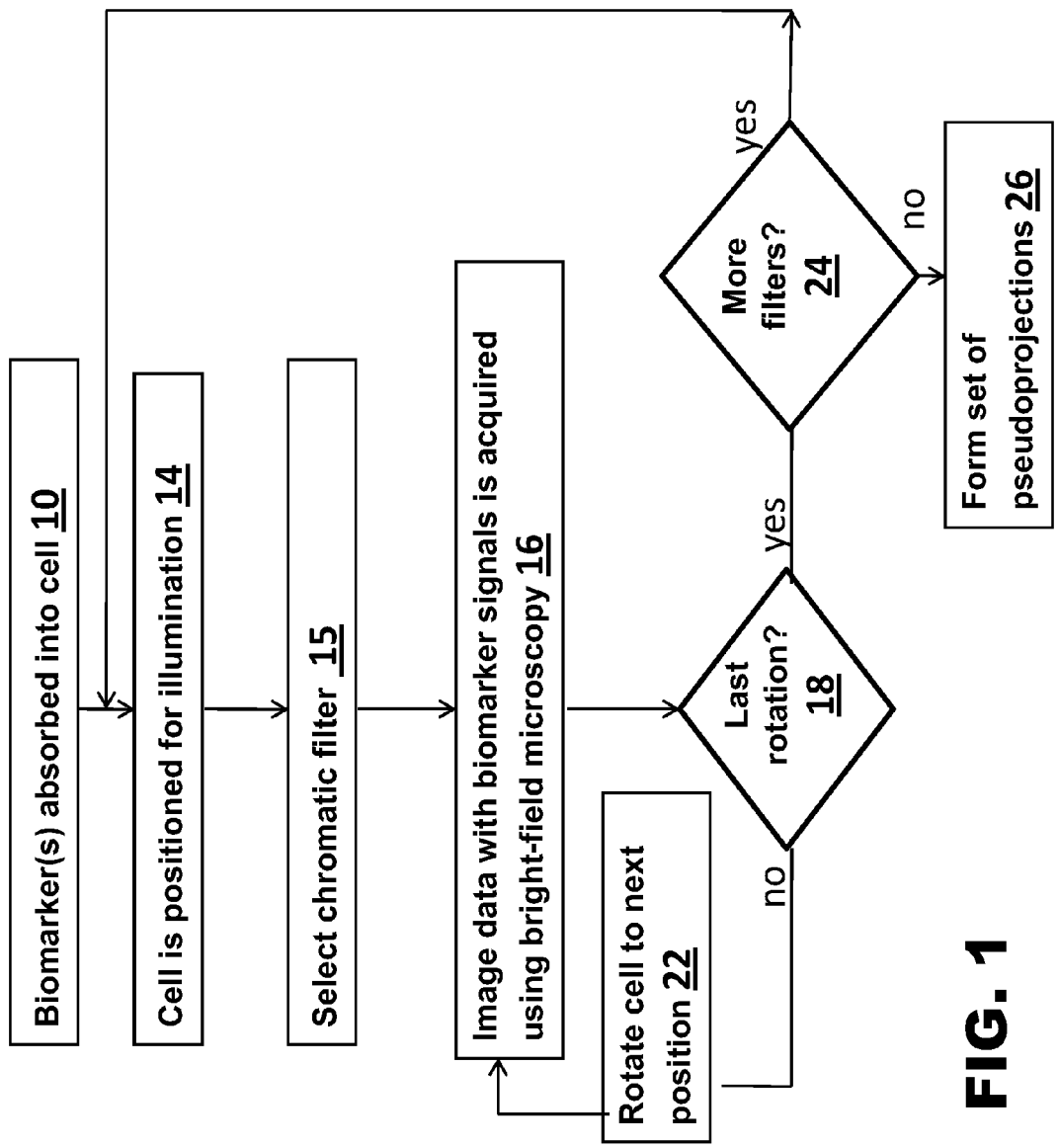
FIG. 1 schematically shows an example of a method for 3D imaging of cells in an optical tomography system employing biomarkers and bright-field microscopy.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE PREFERRED EMBODIMENTS

The following disclosure describes several embodiments and systems for imaging an object of interest. Several features of methods and systems in accordance with example embodiments are set forth and described in the Figures. It will be appreciated that methods and systems in accordance with other example embodiments can include additional procedures or features different than those shown in Figures. Example embodiments are described herein with respect to biological cells. However, it will be understood that these examples are for the purpose of illustrating the principles of the invention, and that the invention is not so limited.

Additionally, methods and systems in accordance with several example embodiments may not include all of the features shown in these Figures. Throughout the Figures, like reference numbers refer to similar or identical components or procedures.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or various combinations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

DEFINITIONS

Generally as used herein the following terms have the following meanings when used within the context of optical microscopy processes. The following definitions are provided to promote understanding of the disclosure and are not to be considered limiting:

"Bright-field microscopy" is a microscopy method in which contrast (differences in light intensities) is generated by variations in the refractive index and absorbance of the light passing through the specimen. As a result, the image appears as dark objects within a bright background. This technique is accomplished by collecting substantially all the light scattered below a maximum angle relative to the incident light. Typically, a bright-field microscope employs a condenser that focuses light into a cone whose apex is in the specimen plane, and an objective that collects substantially all the light scattered at angles less than ($NA_{cond}+NA_{obj}$), where $NA_{cond}$ and $NA_{obj}$ are the numerical apertures of the condenser and the objective, respectively.

"Capillary tube" has its generally accepted meaning and is intended to include transparent microcapillary tubes and equivalent items with an inside diameter of 500 microns or less.

"Dark-field microscopy" is a microscopy method that does not capture the unscattered light that passes through the specimen plane. Contrast is generated by the presence of high-angle scattered light, so the image appears as bright objects in a dark background. The objective captures only light scattered by the specimen above a minimum scattering angle, relative to the incident light. This is typically accomplished by obscuring the central part of the condenser lens, so that the incident light forms a hollow cone whose apex is in the specimen plane. The objective lens collects only light emitted at angles less than the angular size of the obscuring disk in the condenser lens. Typically, the light is incident on the specimen plane at angles between $NA_{dark}$ and $NA_{cond}$, and the objective collects light at angles less than $NA_{obj} < NA_{cond}$, where $NA_{dark}$, $NA_{cond}$, and $NA_{obj}$ are the numerical apertures corresponding to the angular width of the condenser's central obscuration, the condenser lens, and the objective lens, respectively.

"Depth of field" is the length along the optical axis within which the focal plane may be shifted before an unacceptable image blur for a specified feature is produced.

"Object" means an individual cell or other entity.

"PRET" refers to Plasmon Resonant Energy Transfer, a method of amplified light scattering described recently by Liu et al., "Quantized Plasmon Quenching Dips Nanospectroscopy Via Plasmon Resonance Energy Transfer" (Nature Methods, vol. 4, no. 12, December 2007, pp. 1015-1017), the disclosure of which is incorporated by reference. PRET employs a dark-field microscope and nanoparticles onto which molecules have been adsorbed in a substantially irreversible manner. By illuminating the nanoparticles with white light, a wide scattering peak is generated; the spectral location, amplitude, and shape of the scattering peak are characteristic of the metal used and the size of the nanoparticles. For example, gold nanoparticles having diameters of approximately 30 nm, the scattering peak is around 575 nm, with a width (full-width at half-maximum) of about 100 nm. The presence of the molecules adsorbed to the surface causes dips in the scattering peak at the wavelengths where the adsorbed molecules exhibit spectroscopic absorption bands. By adsorbing functionally-specific molecules that act as biomarkers onto the nanoparticles allowing them to penetrate the cellular and/or nuclear envelopes of a biological cell, and detecting the colors of the resultant scattered light using dark-field microscopy, the spatial locations of specific molecular and/or functional features can be identified.

"Processor" and "computer processor" encompass a personal computer, a microcontroller, a microprocessor, a field programmable object array (FPOA), a digital signal processor (DSP), an application-specific integrated circuit (ASIC), a field programmable gate array (FPGA), a programmable logic array (PLA), or any other digital processing engine, device or equivalent.

"Pseudo-projection" includes a single image representing a sampled volume of extent larger than the native depth of field of the optics.

"Specimen" means a complete product obtained from a single test or procedure from an individual patient (e.g., sputum submitted for analysis, a biopsy, a nasal swab or other biological material). A specimen may be composed of one or more objects. The result of the specimen diagnosis becomes part of the case diagnosis.

"Sample" means a finished cellular preparation that is ready for analysis, including all or part of an aliquot or specimen.

Color Imaging

A common technique for functional imaging of cells is to treat them with labeled molecules. These biomarkers are typically either fluorophores or chromophores. A fluorophore re-emits radiation at a wavelength close to the wavelength of the incident light, whereas a chromophore absorbs specific wavelengths of incident light. Using a single camera, for example, an RGB color camera, or equivalent has the advantage of ensuring the optimum spatial synchronization of the separate color signals.

The present disclosure allows an extension of optical projection tomography to provide information about the cell structure at the functional and molecular level. As described in detail below, this may be accomplished by first preparing the cells with multiple stains, molecular labels or biomarkers, and/or embedded nanoparticles, and by employing bright-field, fluorescent, or dark-field imaging, coupled with molecular quenching of bulk plasmons, chromatic notch filters, color cameras, multiple monochrome cameras and equivalents. These methods may permit live cell imaging, and thus they are expected to advance cell analysis, drug development, and related fields.

As noted above, fluorescence presents a problem for conventional tomography, since it means there is a light source within the reconstruction volume, along the projection path. In contrast, fluorescence does not present the same problem for optical projection tomography, because it relies on pseudo-projections rather than true projections. The pseudo-projections are formed by collecting the scattered and emitted light, and focused onto a detection element.

Referring now to FIG. 1, an example of a method for 3D imaging of cells in an optical tomography system employing biomarkers and bright-field microscopy is schematically shown. In one embodiment, the subcellular structure of a biological object, such as a cell, is labeled by introducing at least one nanoparticle-biomarker where, for example, biomarkers are absorbed into a biological cell 10. The cell may then be positioned for illumination 14 relative to a microscope objective to present varying angles of view by rotating the cell. The labeled biological object is illuminated with radiation having wavelengths between 150 nm and 900 nm so that the at least one nanoparticle-biomarker is selected to emit or absorb radiation having wavelengths between 150 and 900 nm. A selected narrow-band chromatic filter which is a member of a set of filters, may then be introduced into the optical path 15 to produce filtered signals within a set of wavelength bands. The filtered signals transmitted through the labeled biological object and the microscope objective within the set of wavelength bands are sensed to produce image data using bright-field microscopy 16. After the image data is acquired, a determination is made under computer control as to whether image data from all angles of view of the cell have been acquired as indicated when the last rotation of the cell has been completed 18. Otherwise the cell is rotated to the next viewing position 22. The above steps are repeated until a set of image data from varying angles of view has been produced. If the cell rotation is complete, a determination is made as to whether more filters from the set of filters are to be applied 24. If a complete set of filters has been applied a plurality of cross-sectional images of the biological object are formed from the set of image data 26. The plurality of cross-sectional images typically comprises pseudo-projections. In the case of the biological object being a cell, the plurality of cross-sectional images may be reconstructed to form a 3D image of the cell. In an alternate example, the complete set of filters may be applied each time the cell is rotated until all desired views have been imaged at the plurality of filtered bandwidths. In the alternative case the cell undergoes only a single rotation cycle. Other combinations of applying filters and acquiring images are evident from this disclosure and such combinations are considered to be equivalent.

In example embodiments the cell may be live or fixed. The biomarkers can be fluorophores, stained nanobeads, labeled nanobeads, biological molecules, nanoparticles, metallic nanoplasmonic particles, silver nanoparticles, gold nanoparticles, synthetic nanoparticles, dielectric polystyrene nanoparticles, quantum dots, chromophores, or any combination of these and equivalents. The signal bandwidth generated by illuminating the biomarkers with electromagnetic radiation, including light, may be wide or narrow, relative to the detection bandwidth or bandwidths.

Figure 2:
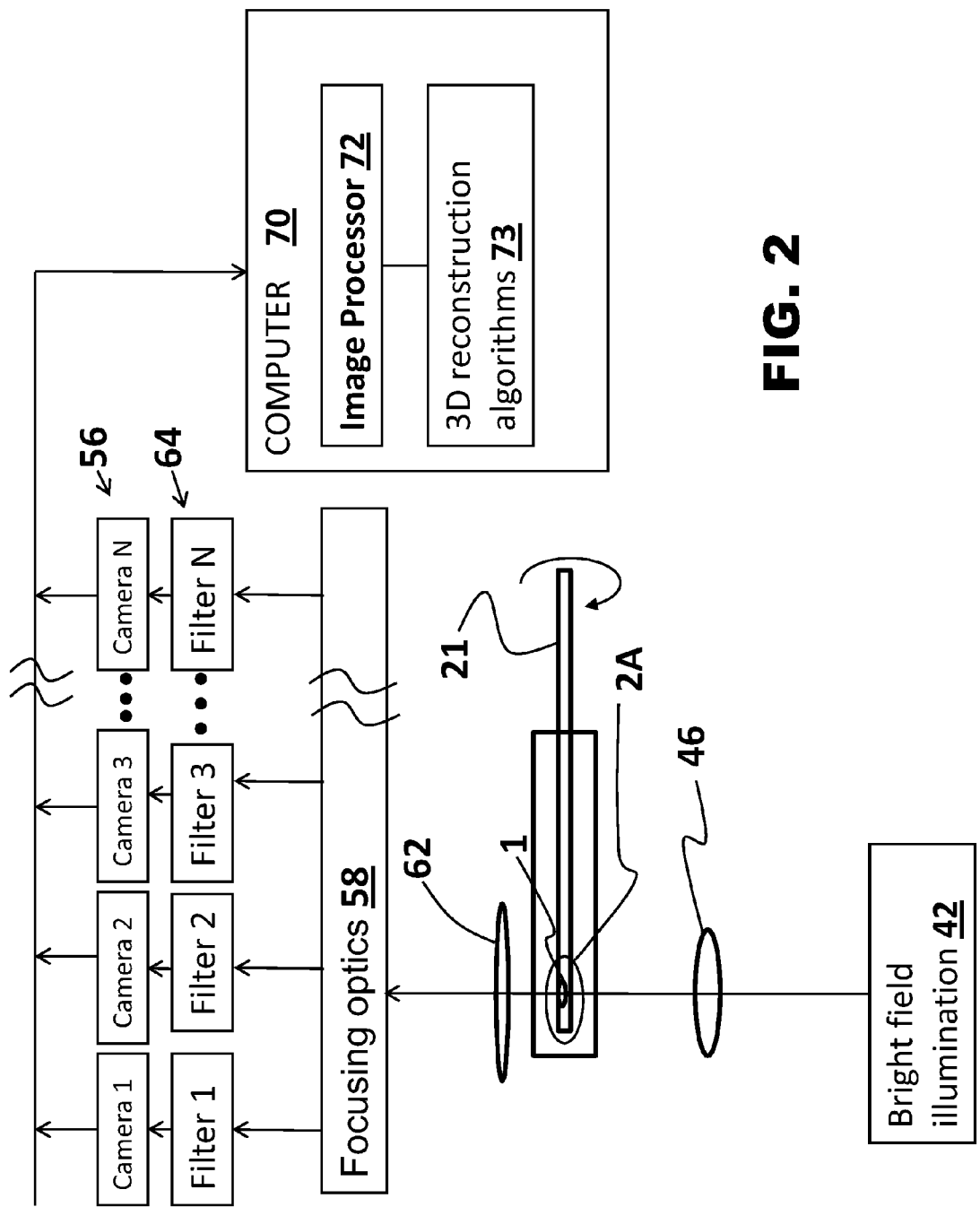
FIG. 2 schematically shows an example of an optical tomography system employing a plurality of cameras and bright-field microscopy.

Referring now to FIG. 2, an example of an optical tomography system employing a plurality of cameras and bright-field microscopy is schematically shown. Included are a bright-field illumination source 42, condenser lens 46, objective lens 62, and focusing optics 58. A set of narrow-band filters 64 are located to filter light reaching the plurality of cameras 56. An apparatus, such as a rotating capillary tube 21, is held in position to present varying views of an object 1 contained in the apparatus in the field of view of the objective lens 62. Each of the plurality of cameras 56 is coupled to provide imaging data to a central processing unit, such as a personal computer 70 or the like.

The computer 70 may advantageously be configured to run software programs as included in an image processor 72 coupled to a reconstruction module 73, where the reconstruction module processes image data to form a 3D image of the cell. The focusing optics 58 may comprise a conventional design including focus lenses and beamsplitters arranged to transmit light to the plurality of filters and cameras. The set of narrow-band filters 64, are here further designated as FILTER 1-FILTER N, where N represents an integral number. Similarly the plurality of cameras 56 are further designated Camera 1-Camera N. Thus the filters or cameras may comprise any useful number.

The cell may be embedded in an optically clear gel and injected into a microcapillary tube, which can be mechanically rotated between two clear, flat surfaces, such as a microscope slide and a coverslip. The interstices between the glass components are filled with refractive-index-matching fluid, such as optical oil available from, for example, Cargille Laboratories, Cedar Grove, N.J. In an alternative embodiment the cell may be held in a fluid environment instead of a gel. Alternative methods may be employed to obtain views of the cell at varying angles. Further details are taught in Fauver and Nelson, "Optical Projection Tomography Microscope," U.S. patent application Ser. No. 10/975,162, published on May 11, 2006 as US Publication No. 2006-0096358-A1, and incorporated herein by reference. Another useful method for obtaining multiple views using a rotating capillary tube is disclosed in U.S. patent application Ser. No. 11/678,316 to Hayenga published on Aug. 28, 2008 as US Publication No. 2008-0205739-A1 entitled "Fluid Focusing for Positional Control of a Specimen For 3-D Imaging," the teachings of which are incorporated herein by reference.

The biomarker signals are detected using a bright-field microscopy setup incorporating a sequence of one or more narrow-band chromatic filters. In one example, a set of narrow-band chromatic filters are mechanically exchanged. Alternatively, an electronically tunable chromatic filter or equivalent devices may be employed. Electronically tunable filters are commercially available from, for example, CRI, Inc., of Woburn, Mass., and include tunable RGB filters. One type of commercially available tunable filter, for example, allows bandwidths as small as 0.25 nm (FWHM), and requires as little as 150 ms to change the center wavelength. Such tunable RGB filters provide filter band-passes of 100 nm FWHM in the red, green, and blue wavelengths, and can change the passband in as little as 2 ms.

The narrow-band filters provide sufficient contrast between regions where the biomarkers are present and regions where they are absent. Each filter is, preferably, optically transparent in the absorption wavelengths of at least one of the biomarkers. Detection by two or more filters is acceptable, as long as the biomarker still provides an identifiable color signature in the composite image that results from combining the separated color signals. One or more sequences of pseudo-projections, one for each narrow-band filter employed, are acquired in bright-field as the tube rotates through at least 180 degrees. Other useful filters include Bayer filters comprising a color filter array, color filter mosaic or equivalents.

In this embodiment, an additional sequence of pseudo-projections acquired in bright-field from a wide range of wavelengths is acquired simultaneously with the narrow-band pseudo-projections. The images that make up this sequence of pseudo-projections are brought into spatial alignment after acquisition, using one or more computer programs as taught in, e.g., Rahn and Nelson, "Method for Correction of Relative Object-Detector Motion between Successive Views," U.S. Pat. No. 7,260,253 issued Aug. 21, 2007 which is incorporated by reference. The narrow-band pseudo-projections are in general not suitable for providing a spatial reference, as they typically do not provide enough gross detail about the cell to determine the its location with sufficient precision.

As the wideband pseudo-projections are aligned spatially, a record is made of the shifts in the pixel locations necessary to do so. The same shifts are then applied to the narrow-band pseudo-projections, thereby bringing them into spatial alignment, as required to obtain an accurate tomographic reconstruction.

A tomographic reconstruction is computed for each sequence of spatially aligned pseudo-projections using, for example, a computer program applying filtered backprojection for parallel-beam data. The resulting reconstructions can be combined or overlaid to provide spatial information concerning the molecular and/or functional structures within the cell.

In another embodiment, a plurality of biomarker signals are detected with a bright-field microscopy configuration and a sequence of one or more wideband chromatic filters are inserted into one or more optical paths. In this embodiment, the biomarkers may be selected to emit wideband signals. The wideband signals will produce image data that may be formed into wideband pseudo-projections. One of the wideband pseudo-projections can serve as the reference point for the others for purposes of spatially synchronizing them, an additional sequence of pseudo-projections may be used, or separate pseudo-projections may be combined digitally to provide the pseudo-projections necessary for spatial registration.

Figure 2A:
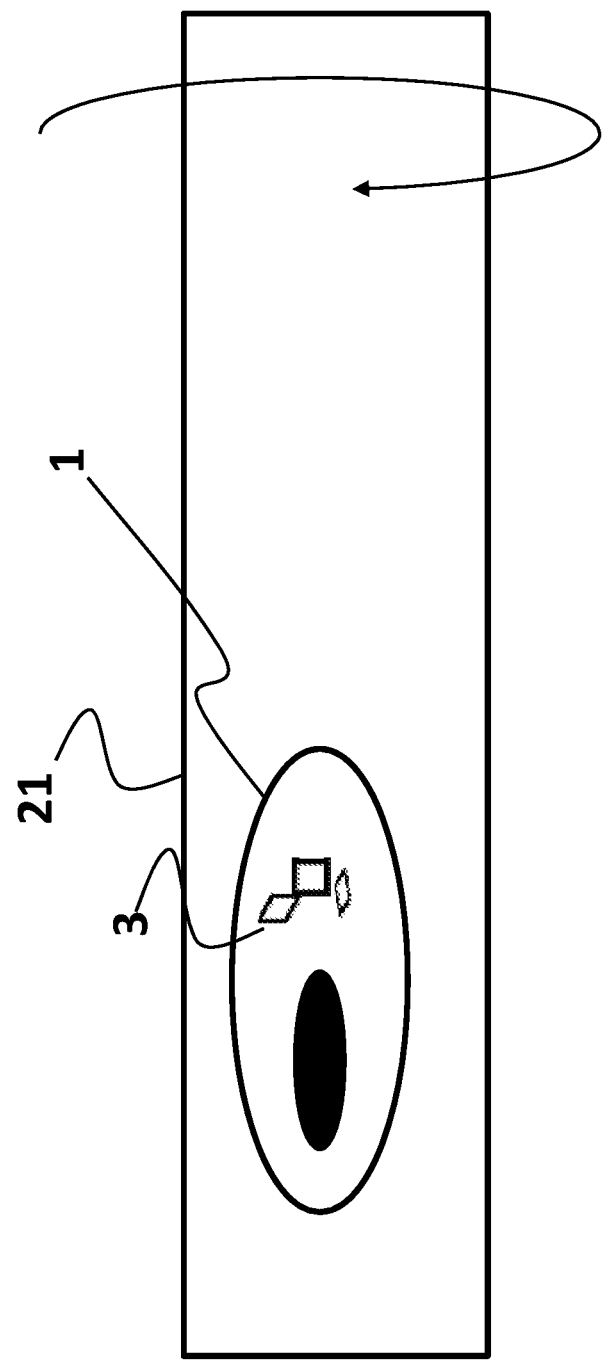
FIG. 2A schematically shows a more detailed view of a cell including a plurality of biomarkers in an example of a method for 3D imaging of cells in an optical tomography system employing a plurality of cameras and bright-field microscopy.

Referring now to FIG. 2A, a more detailed view of a cell including a plurality of biomarkers in an example of a method for 3D imaging of cells in an optical tomography system employing a plurality of cameras and bright-field microscopy is schematically shown. In one useful example, the microcapillary tube 21 holds the object 1 that comprises a cell treated with two or more biomarkers 3. The two or more biomarkers 3 have signal bandwidths that may be wide or narrow, relative to the detection bandwidth or bandwidths. In one example of this embodiment, the biomarkers comprise three types of stained nanobeads 3, each type absorbing in a separate narrow range of wavelengths as described below.

Figure 3:
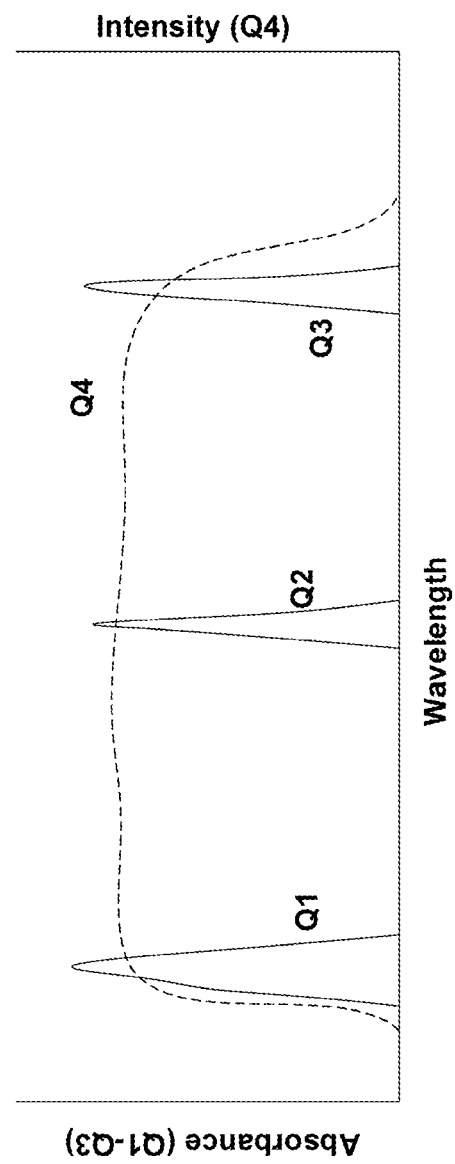
FIG. 3 schematically shows an example of wavelength-dependent signals in a system for 3D imaging of cells in an optical tomography system employing a multi-color camera and a bright-field microscopy configuration.

Referring now to FIG. 3, an example of optical absorbance spectra in a system for 3D imaging of cells is schematically shown. Here a plurality of biomarkers, such as stained nanobeads or similar devices absorb light in a plurality of narrow band wavelength ranges designated Q1, Q2, and Q3. For example, Q1 may comprise wavelengths between 490 and 495 nm, Q2 may comprise wavelengths between 510 and 515 nm, and Q3 may comprise wavelengths between 530 and 535 nm. The cells are embedded in gel and inserted into a tube as described before. The biomarkers are illuminated with wideband light having an intensity spectrum Q4.

In one example, using a configuration substantially similar to the embodiment shown in FIG. 2, four monochrome cameras are used. A bright-field microscope collects bright-field pseudo-projections while the tube is rotated within the cameras' fields of view. Those skilled in the art and having the benefit of this disclosure will understand that the terms "narrow-band" and "wideband" are not limited by the above example, but are relative to each other and the bandwidth of the light sensor detection range.

The light collected by the optics may be split into four separate paths. A first path allows wideband light to reach a first camera. The other three paths each include a narrow-band chromatic filter, where each filter allows only light from one of the plurality of wavelength ranges Q1, Q2, or Q3 to be transmitted. Thus, a second camera is sensitive only to light within the range Q1, a third camera is sensitive only to light within the range Q2, and a fourth camera is sensitive only to light within the range Q3.

The wideband-sensing first camera provides a spatial reference for the other pseudo-projections, as described herein. The pseudo-projections from the other cameras are spatially registered and overlaid to provide detailed information about the locations of each type of stained nanobead. If the stained nanobeads have been conjugated with labels, then their locations further provide information about the composition or function of the sub-cellular structures.

Figure 4:
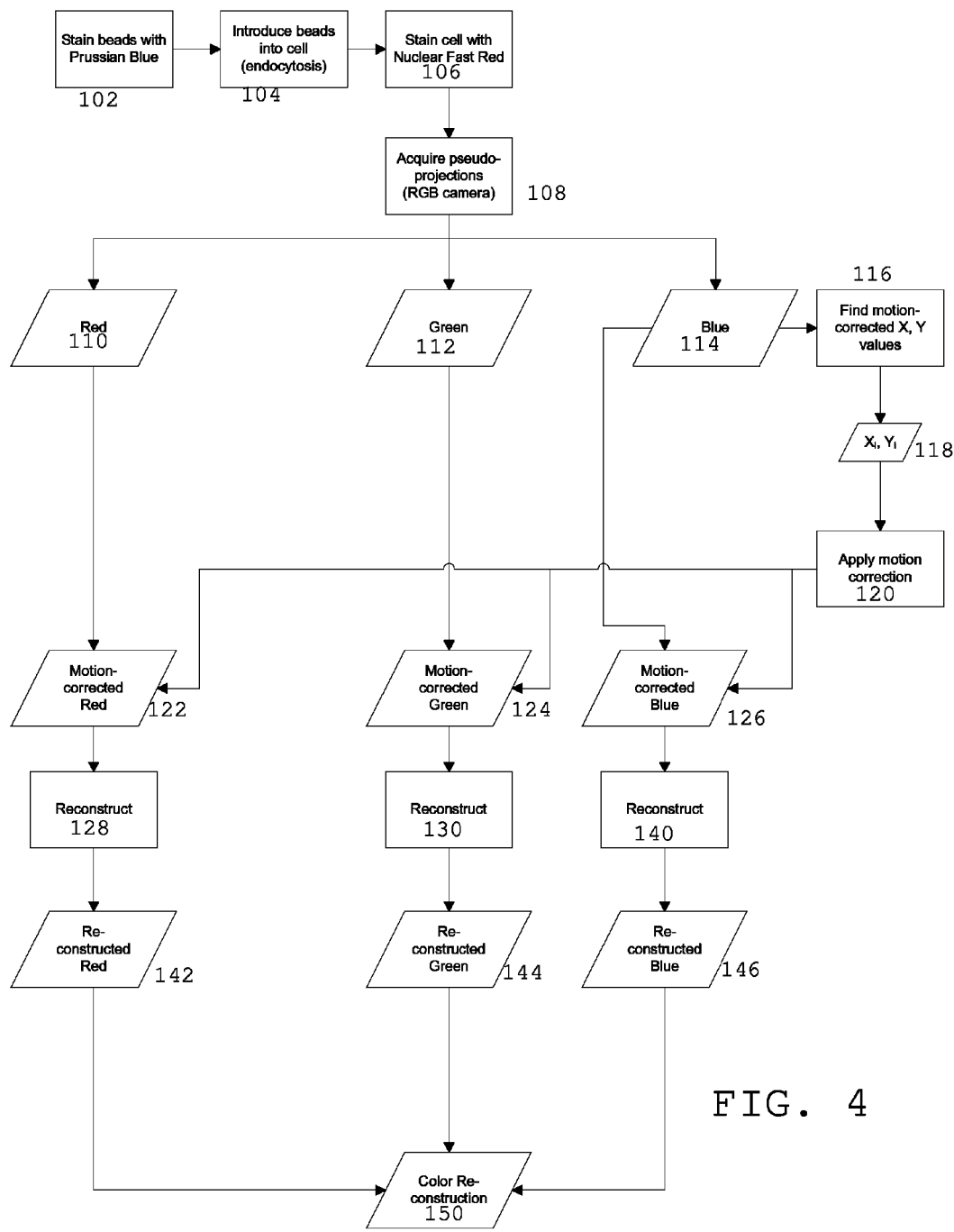
FIG. 4 schematically shows an example of a system for 3D imaging of cells in an optical tomography system employing a multi-color camera and using motion-corrected X,Y values.

In FIG. 4 an example of a system for 3D imaging of cells in an optical tomography system employing a color camera and using horizontal (X) and vertical (Y) motion-correction values is schematically shown. In one example of this embodiment, nanobeads are treated with a stain 102, and introduced into an aqueous solution containing live cells 104. The nanobeads are taken into the cell's cytoplasm via endocytosis. The cells are then fixed and treated with a nuclear counterstain 106. The cells are embedded in an optically clear gel and inserted into a microcapillary tube as described above. The tube is brought into the field of view of a bright-field microscope. It is rotated through at least 180 degrees while magnified, bright-field pseudo-projections are acquired at multiple viewing perspectives using a standard three-color (RGB) camera 108. The color channels are separated from the RGB pseudo-projections into three monochrome pseudo-projections, for example, red 110, green 112 and blue 114. In one example the nanobeads may comprise commercially available ferumoxide injectable solution or equivalents.

Another example of a useful stain is Prussian blue stain, having an absorbance peak of about 680 nm, or equivalent materials. While variations may be commercially available, typically it is made as an inorganic compound. One useful nuclear counterstain is, for example, nuclear fast red counterstain or equivalents having an absorption peak ranging from 460-550 nm. Prussian blue stain and nuclear fast red counterstain are commercially available.

One of the color channels is selected to provide the spatial reference. Preferably, the selected channel will be the color channel that generates images having a balance between cellular detail and gross cellular features, so as to provide a large number of cues on which the motion-control algorithm can focus. In an example embodiment, the preferred channel is the blue channel, as it corresponds to the nuclear fast red's absorption peak, and thus the images contain high contrast of features throughout the nucleus. The nanobeads may accumulate in too small a volume, or may be too opaque, to permit accurate spatial registration in the red channel where their absorption peak is located. The green channel may lack sufficient contrast. Motion-corrected X, Y values are generated from the blue pseudo-projections 116. The generated motion-corrected values $X_i$, $Y_i$ are generated for each pseudoprojection 118 and applied to each color channel 120. Motion corrected pseudo-projections are produced for the red channel 122, green channel 124 and blue channels 126.

Using a processor to execute the 3D reconstruction software program module, the pseudo-projection images from each spatially-registered color channel can then be reconstructed separately 128, 130 and 140 and the results 142, 144 and 146 can be overlaid and combined to form a color (RGB) 3D reconstruction 150. Since the different colors are spatially registered due to the immobility of the separate color-sensing pixels in the camera array, the 3D reconstruction contains information about the cellular composition in addition to its structure. Since the different colors are spatially registered they are also synchronized. Information about the cellular composition is substantially found in the narrow-band optical densities, while structure is substantially characterized by wideband optical density.

Figure 5:
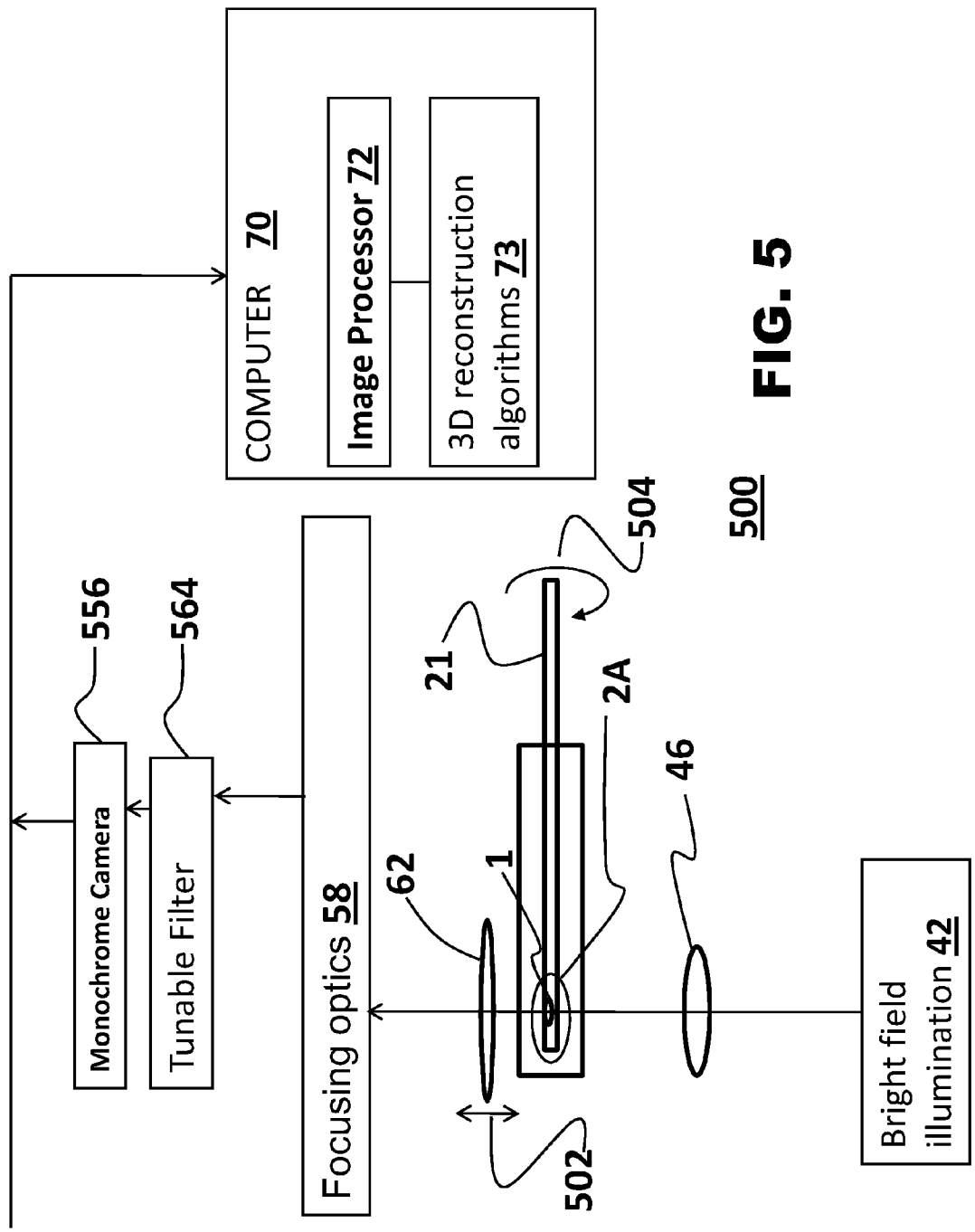
FIG. 5 schematically shows an example of an optical tomography system employing a monochrome camera and electronically tunable filter.

Referring now to FIG. 5, an example of an optical tomography system employing a monochrome camera and electronically tunable filter is schematically shown. The optical tomography system 500 may advantageously comprise an axial translation mechanism 502 coupled to translate the objective lens 62 through a scanning range so as to extend the depth of field. A rotating mechanism 504 is coupled to a tube 21 for turning the object of interest to present a plurality of different views to the objective lens 62. At least one chromatic filter 564 is inserted into at least one optical path. At least one camera 556 may be positioned to receive light radiation transmitted through the labeled biological object 1 and the microscope objective 62. An image processor 72 is coupled to receive data from the at least one camera 556, where the image processor 72 generates image data. A reconstruction module 73 is coupled to the image processor 72, where the reconstruction module processes the image data to form a 3D image of the cell.

In operation, one or more biomarkers are inserted into a cell 1, and the cell 1 is inserted into a rotatable microcapillary tube 21. The biomarkers may emit signals exhibiting wide or narrow signal bandwidths, relative to the detection bandwidth or bandwidths. The emissions may be fluorescent. The at least one camera 556 may advantageously be a single monochrome camera. As the microcapillary tube 21 rotates through a plurality of angles, an electronically tunable filter 564 as, for example discussed above, sweeps through one or more narrow-band ranges and one wideband range at each angle, while the single monochrome camera 556 acquires two or more bright-field pseudo-projections, one corresponding to each wavelength range. Spatial registrations and reconstructions may then be performed as described above.

Figure 6:
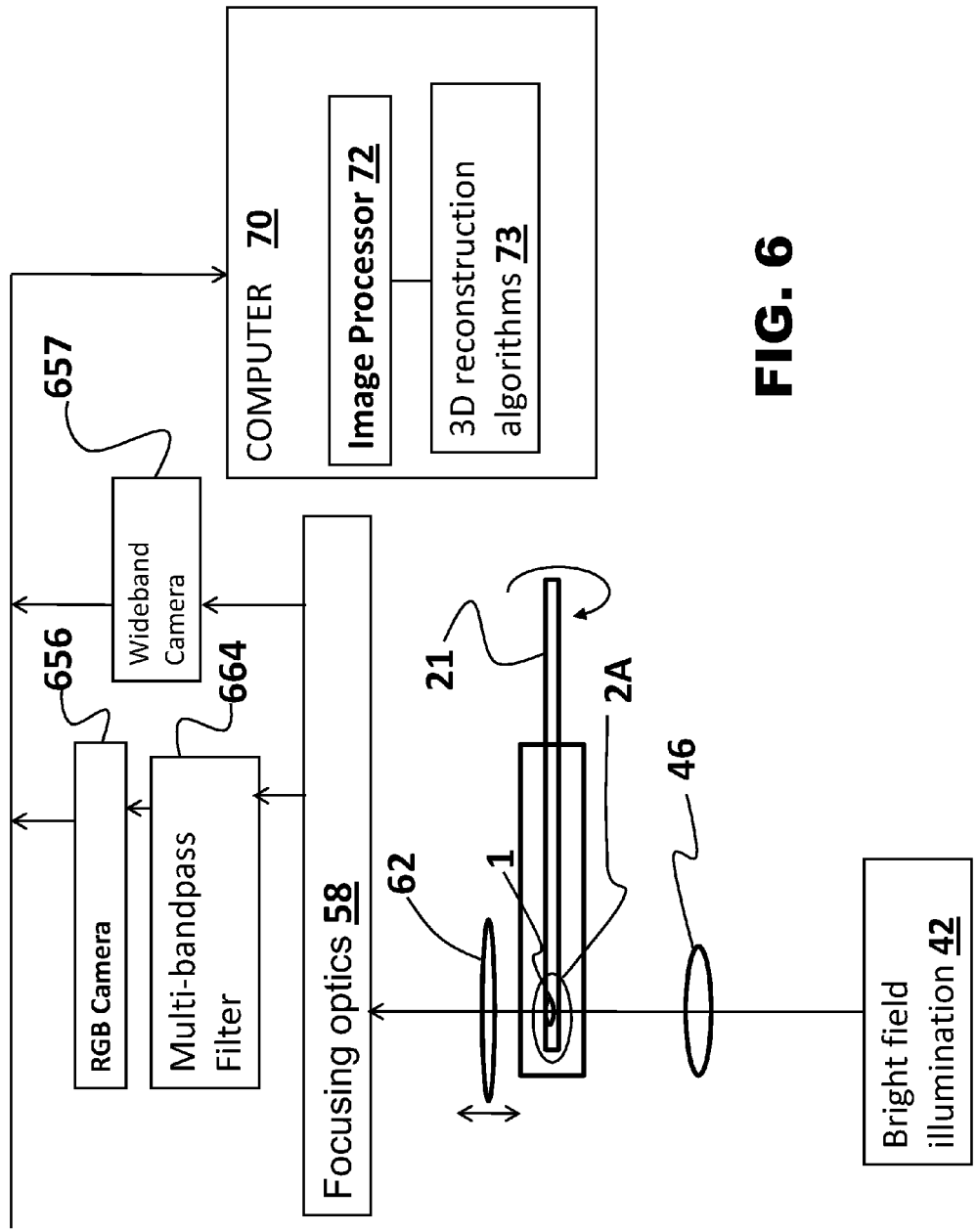
FIG. 6 schematically shows an example of an optical tomography system employing a multi-band-pass filter.

Referring now to FIG. 6 an example of an optical tomography system employing a multi-band-pass filter is schematically shown. One or more biomarkers are inserted into a cell 1, and the cell 1 is inserted into a rotatable microcapillary tube 21, as described above. The biomarkers may advantageously be selected to emit signals having signal bandwidths that may be wide or narrow relative to the detection bandwidth or bandwidths. A single RGB camera 656 collects pseudo-projections in one or more narrow-band ranges, using a multi-band-pass filter 664. A second camera 657 collects wideband, bright-field pseudo-projections while the tube rotates. Spatial registrations and reconstructions may then be performed as described above.

Bulk Plasmons

Figure 7:
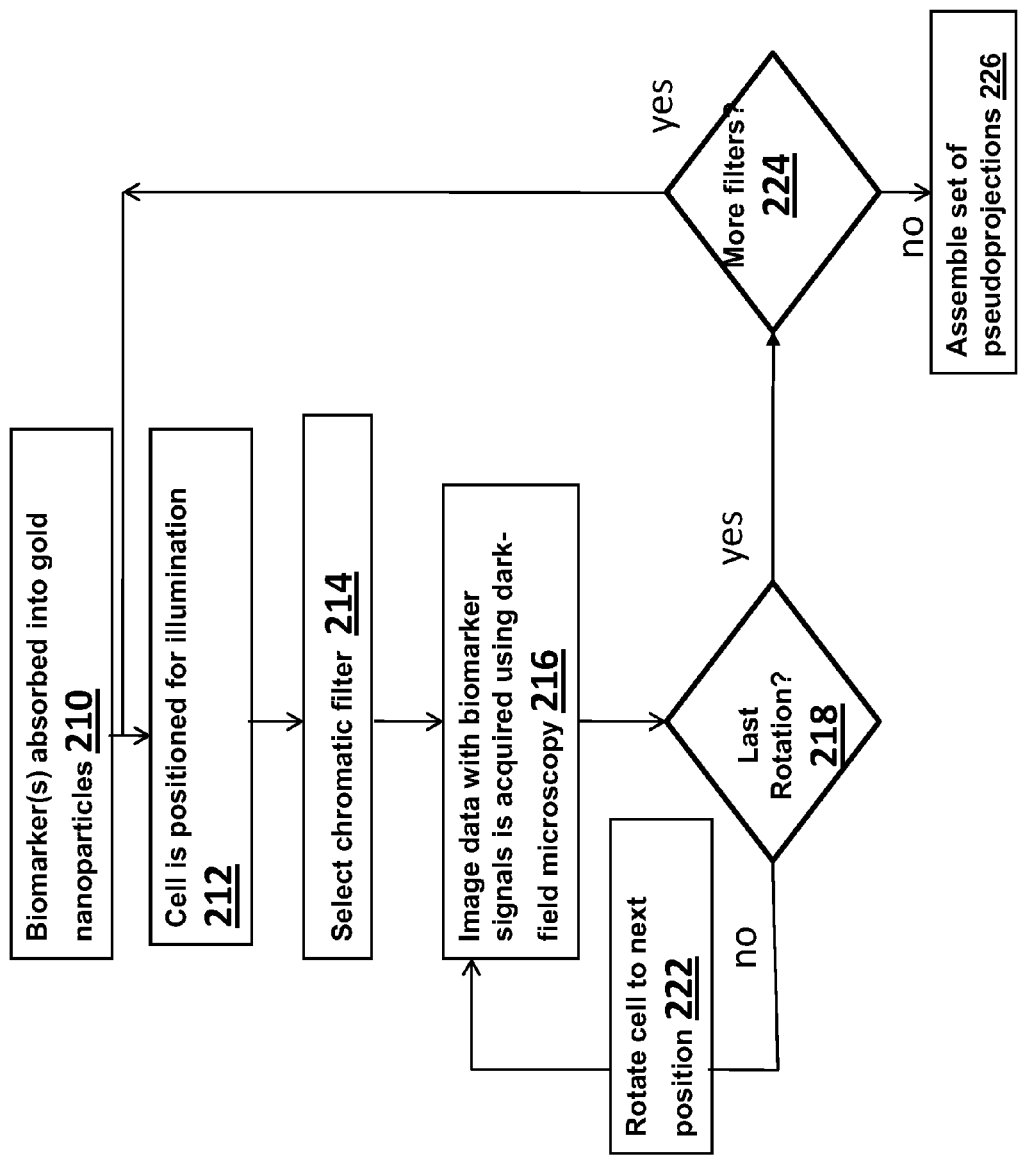
FIG. 7 schematically shows an example of a method for 3D imaging of cells in an optical tomography system employing PRET and dark-field microscopy.

Referring now to FIG. 7, an example of a method for 3D imaging of cells in an optical tomography system employing PRET and dark-field microscopy is schematically shown. A major difficulty with biomarkers is that their signal levels are extremely low. For example, for a fluorescent label the re-emitted light flux may be $10^6$ times smaller than the incident light flux. Even for a very efficient marker, the high specificity required to make it useful means that the density of marker molecules within the cell may be very low. As a result, use of labeling techniques often involves a very low signal level, which could make special imaging configurations such as epi-illumination or dark-field illumination necessary. However, the signal-to-noise ratio of chromophores and fluorophores can be greatly amplified by use of PRET. By coating gold nanoparticles, for example, with biomarkers having strong absorption energies near the plasmon energy, and inserting the gold-coated nanoparticles into a cell and/or cell nucleus, a quenching effect in the plasmon scattering peak can be observed at the wavelengths of the biomarker absorption bands. It is then possible to determine in the composition or function of sub-cellular structures within the cytoplasm or nucleus by detecting the PRET signatures due to one or more of the biomarkers so inserted.

In one example, one or more biomarkers are introduced irreversibly onto gold nanoparticles (diameter 10-40 nm) to form biomarker/nanoparticle assemblies and inserted into at least one biological object of interest to make a labeled biological object of interest, such as, for example, a cell labeled via endocytosis 210. As described above, the optical tomography system includes at least one illumination source for producing light having a spectral bandwidth with wavelengths between 150 and 900 nm and an objective lens located to receive the light emanating from a labeled region of interest from the biological object. The biological object is positioned for illumination 212 as by, for example, using a delivery device positioned in an optical path relative to a microscope objective, such as by embedding it in an optically non-scattering gel and inserted into a rotatable tube. A sequence of one or more narrow-band chromatic filters is incorporated into the optical path, such that at least one filter corresponds to each biomarker used 214. Image data with biomarker signals, for example, PRET signals are generated and collected by the objective lens 216. In practice, for example, a determination is made under computer control as to whether all angles of view of the cell have been acquired or if the last rotation of the cell has been completed 218. Otherwise the cell is rotated to the next viewing position 222. The above steps are repeated until a set of image data from varying angles of view has been produced. A sequence of narrow-band pseudo-projections, one for each biomarker, is acquired at each angle as the tube rotates through at least 180 degrees. If the cell rotation is complete, a determination is made as to whether more filters from the set of filters are to be applied 224. If a complete set of filters has been applied a plurality of cross-sectional images of the biological object are formed from the set of image data 226. Similar to the method of FIG. 1, the plurality of cross-sectional images typically comprise pseudo-projections. In the case of the biological object being a cell, the plurality of cross-sectional images may be reconstructed to form a 3D image of the cell.

The sequence of filters may be selectively applied by exchanging different narrow-band filters, or by using an electronically tunable chromatic filter, as discussed above. The narrow-band filters provide sufficient contrast between regions where the markers are present and regions where they are absent.

An additional sequence of wideband pseudo-projections may be acquired using bright-field microscopy to provide the spatial reference, as described above for the bright-field embodiments. The pseudo-projections are spatially registered, tomographically reconstructed, and overlaid or otherwise combined similarly to the process discussed above with reference to FIG. 4.

Another embodiment is similar to that previously-described, except that there is a separate optical path for each biomarker and filter, plus one additional optical path for acquiring the wideband pseudo-projections.

Mass Conservation

Figure 8:
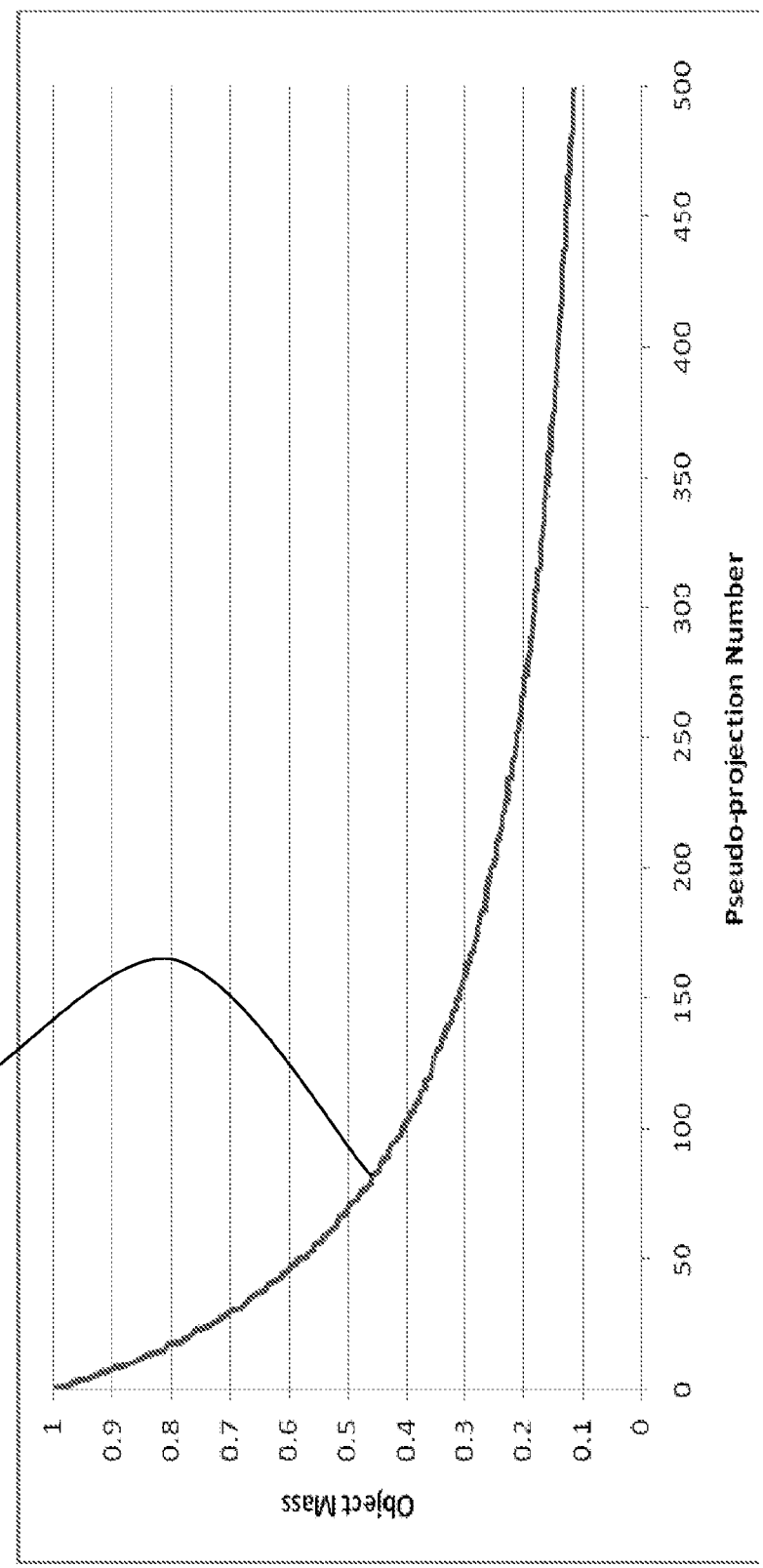
FIG. 8 shows an illustration of the change in an object's mass over the course of 500 pseudo-projections if photobleaching of the object is taking place during the image acquisition.

Another method for ameliorating problems due to photobleaching and other errors that may be present in an optical tomography microscopy system employs principles of mass conservation. Referring now to FIG. 8, an illustration of the change in an object's mass over the course of 500 pseudo-projections if photobleaching of the object is taking place during the image acquisition is shown. The y axis is a scale of object mass and the x-axis is a scale showing pseudo-projection numbers. As reflected by curve 100, object mass decreases in a non-linear fashion as the pseudo-projection number increases. In the example shown, a first pseudo-projection taken at number 0, which may be labeled "pp#0," has a mass of about 1.0. A pseudo-projection acquired at number 490, which may be labeled "pp#490," has a mass approaching 0.1.

Figure 9:
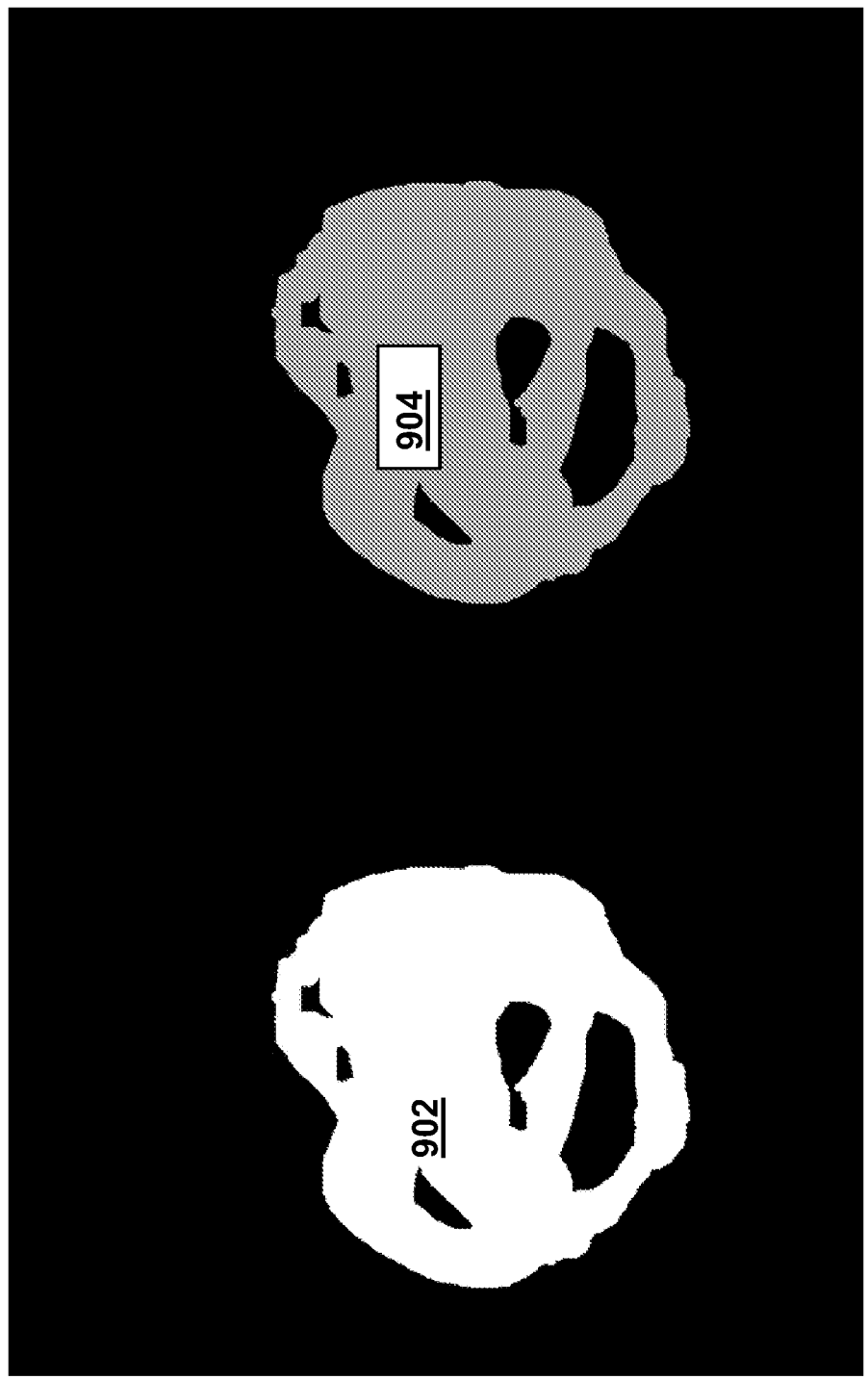
FIG. 9 shows an example of two images having the same object area but different object masses.

Referring now to FIG. 9, an example of two images having the same object area but different object masses is shown. Here, a first image 902 may correspond to a low pseudo-projection number and a second image 904 may correspond to a higher pseudo-projection number. As quantified above and shown visually here, later-acquired pseudo-projection images for the same object, if not corrected, will have a decreased mass due to photobleaching. If the pseudo-projections that are acquired suffer from the effects of photobleaching or poor focus and/or illumination gradients, the tomographic reconstruction will contain distortions of the pixel intensities unless these effects are corrected.

Figure 10:
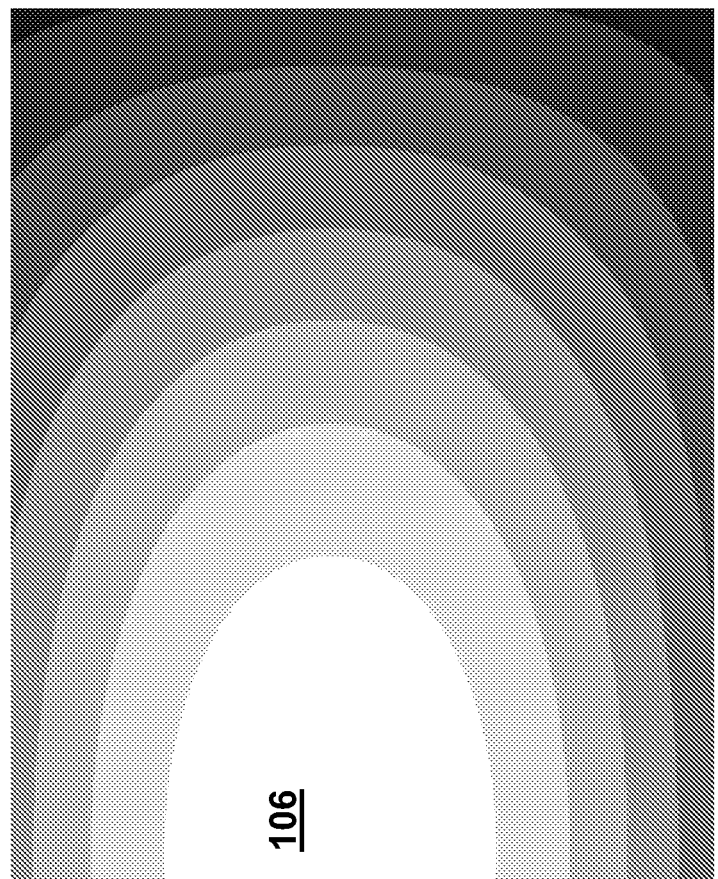
FIG. 10 shows an example of a field of view containing illumination gradients.

Referring now to FIG. 10, an example of a field of view containing illumination gradients is shown. Illumination gradients can be detected and quantified by using, for example, a fluorescent reference material. This standard may consist of a fluorescent microsphere that that has been verified to be non-photobleaching, or it may comprise a sheet of non-photobleaching fluorescent material. By measuring the intensity of the standard at multiple locations across the field of view of the detector, the illumination gradient can be determined. Here image 106 shows the brightest illumination field appearing to the right. Illumination grows progressively dimmer at the left edge of the image 106.

Figure 11:
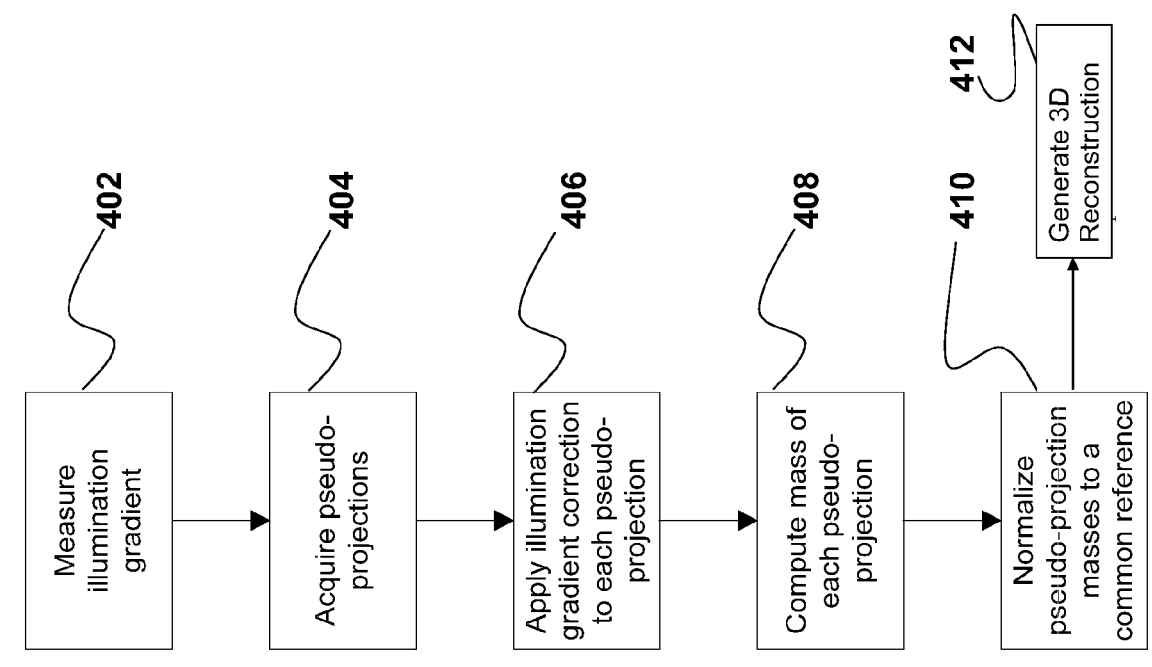
FIG. 11 shows the process of applying mass normalization to a set of fluorescence image data.

Referring now to FIG. 11, an example of a process of applying mass normalization to a set of fluorescence image data is shown in a block diagram form. In one example the process includes optionally measuring an illumination gradient 402, acquiring a set of pseudo-projections 404 of an object, applying illumination gradient corrections to each pseudo-projection if necessary to generate a set of corrected pseudo-projections 406, computing a mass for each of the set of corrected pseudo-projections 408 to generate a set of pseudo-projection mass values, and normalizing the set of pseudo-projection mass values to a common reference 410 to produce a normalized set of pseudo-projection mass values. A 3D image reconstruction of the object is generated from the normalized set of pseudo-projection mass values 412. The process of applying mass normalization is carried out through execution of an algorithm contained in a software program or the like as executed by operation of a computer processor, electronic circuits, analog circuits or equivalent devices.

To correct for illumination gradients known to be present, each pseudo-projection can be corrected, in a pixel-by-pixel manner if necessary, to compensate for the illumination gradients. Once this process is completed, the mass of the fluorescent object can be determined.

The same correction may be applied to all the pixels in the image. In one example the correction is applied according to a formula:

$$I\_ij \rightarrow I\_ij * sum(I\_ref)/(sum(I\_ij)) \quad (1)$$

where $I\_ij$ is the intensity of a single pixel;
$sum(I\_ij)$ is the sum of all the intensities of all the pixels (for i=1 to imax, j=1 to jmax); and
$I\_ref$ is a reference image or set of values.
In this example, $sum(I\_ij)$ and $sum(I\_ref)$ are scalars.

Since each pseudo-projection collects the emitted light from the entire object volume, the mass is expected to remain constant if there is no photobleaching, illumination gradient, or poor focus. For the most accurate computation, the background pixels in each image should be excluded from the summation. This is helpful in the case where the background pixels are not zero, which may be due to, for example, detector noise, stray light, or imperfect filtering of the collected light which allows some backscattering of the illuminating light to reach the detector.

If photobleaching occurs in different proportions to fluorophores in different portions of the object volume, the normalization may produce inaccurate results. A region of high fluorophore concentration may have a larger number of photobleached fluorophores than a region of low fluorophore concentration, but as long as the percentage of photobleached fluorophores is the same in both regions, introduction of this type of error into results should be minimized.

By normalizing the mass of each pseudo-projection to a common value 410, the effect of photobleaching may be minimized. However, it may also amplify noise in the low-mass images, since these images are likely to have a lower signal-to-noise ratio. It isn't necessary to normalize to an absolute scale as long as the images within a data set are normalized to each other. A suitable common reference for normalizing the data is the un-normalized mass of the first image in the data set.

If the variations in mass are caused by poor focus, this method will not restore the loss of spatial resolution, but it will at least equalize the overall intensity. If the illumination gradient is sufficiently small that the illumination difference is negligible across the portion of the field of view occupied by the cell, then normalizing by object mass can improve the accuracy of the reconstructions, without the necessity of applying the pixel-by-pixel correction method described above.

The mass correction method is especially useful for fluorescence, where the background is black, so it doesn't contribute to the object mass. It can also be applied to bright-field images, as long as the background pixels are eliminated from the mass calculation. For bright-field images, reversing the contrast of the images prior to computing the mass will generally produce more accurate results, since doing so tends to give more weight to the darkest regions within the object, which are unambiguously not part of the background.

Figure 12:
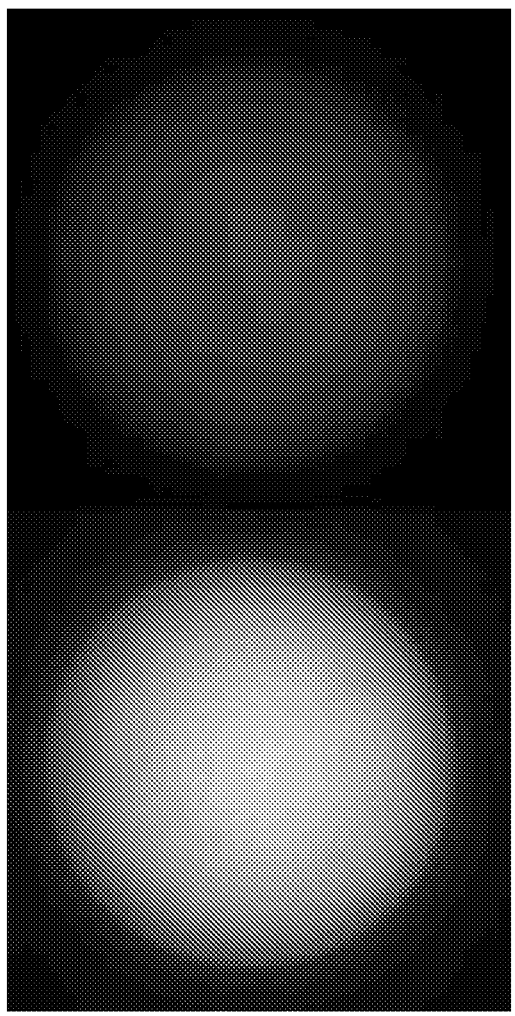
FIG. 12 illustrates two pseudo-projection images of a fluorescent nanobead.

FIG. 12 shows an illustration of two pseudo-projection images of a fluorescent nanobead. Image 12A is an actual pseudo-projection image. Image 12B is a digital alteration of 12A. Image 12A at the left illustrates an image taken at the beginning of the data acquisition (pp#0). Image 12B on the right simulates an image taken late in the data acquisition (pp#490), and demonstrates the effect of photobleaching that has occurred since the start of the acquisition. No mass correction has been applied.

Figure 13:
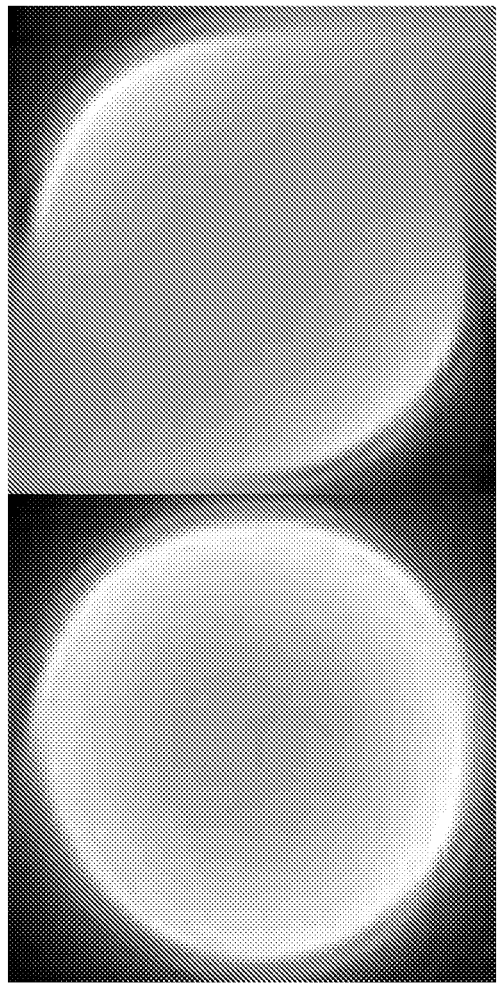
FIG. 13 shows two reconstructions of a nanobead.

FIG. 13 shows two reconstructions of a fluorescent nanobead. FIG. 13A was reconstructed using the set of 500 real pp's of which image 13A is a member. Image 13B was made by digital alteration of the set of pseudo-projections used to make image 13A. Image 13A on the left is a simulated reconstruction in the absence of photobleaching as reconstructed through application of the new method of mass correction described herein. In comparison, image 13B on the right is a simulated reconstructed image without mass correction in the presence of photobleaching. Comparing the two figures reveals how details and clarity are improved using mass correction techniques as discussed above.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, and devices, and that various modifications, both as to the equipment details and operating procedures, may be accomplished without departing from the true spirit and scope of the present invention.

What is claimed is:

1. A method for 3D imaging of a biologic object in an optical tomography system comprising:
   (a) labeling a subcellular structure of the biological object by introducing at least one nanoparticle-biomarker;
   (b) positioning the labeled biological object relatively to a microscope objective to present varying angles of view;
   (c) illuminating the labeled biological object with radiation having wavelengths between 150 nm and 900 nm so that the at least one nanoparticle-biomarker is selected to emit or absorb radiation having wavelengths between 150 and 900 nm, and wherein illuminating employs plasmon resonance energy transfer (PRET), wherein the employment of PRET comprises:
      (i) using a dark-field microscopy configuration, wherein light scattered at high angles relative to the incident light is collected by the objective lens; and
      (ii) incorporating into the biological object at least one ensemble of metallic nanoparticles, each ensemble of metallic nanoparticles having at least one substantially identical labeling molecule attached to the surface of substantially each nanoparticle that is a member of the at least one ensemble of metallic nanoparticles;
   (d) filtering a portion of the produced radiation using a set of filters to produce filtered signals within a set of wavelength bands;

(e) sensing the filtered signals transmitted through the labeled biological object and the microscope objective within the set of wavelength bands to produce image data;
(f) repeating steps (b) through (e) until a set of image data from varying angles of view has been produced; and
(g) forming a plurality of cross-sectional images of the biological object from the set of image data; and (h) reconstructing the plurality of cross-sectional images to form a 3D image of the labeled biological object.

2. The method of claim 1 wherein the set of filters includes at least one filter selected from the group consisting of chromatic filters, narrow-band filters, electronically tunable filters, color filter arrays, color mosaic filters, and wideband filters, at least one edge filter, a notch filter, a sequence of narrow-band filters, a multiple-band filter, an RGB filter, and a Bayer filter.

3. The method of claim 1 wherein filtering comprises selecting a narrow-band filter from the set of filters to produce a set of narrow-band wavelength bands for each of the varying angles of view.

4. The method of claim 1 wherein the set of wavelength bands range from 0.25 nm full width at half maximum (FWHM) to 100 nm FWHM.

5. The method of claim 1 wherein the biologic object includes a biological object selected from the group consisting of a live cell, a human cell, a cancer cell and a fixed cell.

6. The method of claim 1 wherein the at least one nanoparticle-biomarker includes a biomarker selected from the group consisting of fluorophores, stained nanobeads, labeled nanobeads, biological molecules, nanoparticles, metallic nanoplasmonic particles, silver nanoparticles, gold nanoparticles, synthetic nanoparticles, dielectric polystyrene nanoparticles, quantum dots, chromophores, narrow-band fluorophores, and narrow-band chromophores.

7. The method of claim 1 wherein the emitted or absorbed radiation comprises radiation selected from the group consisting of wideband radiation and narrow-band radiation relative to the set of wavelength bands sensed.

8. The method of claim 1 wherein the set of filters comprises at least one filter that is optically transparent in the absorption wavelengths of at least one of the nanoparticle-biomarkers.

9. The method of claim 1 wherein forming a plurality of cross-sectional images comprises forming a sequence of pseudo-projections for each filter that is a member of the set of filters.

10. The method of claim 1, wherein the cross-sectional images include a plurality of wideband pseudo-projections having a set of wideband pixel locations and a plurality of narrow-band pseudo-projections having a set of narrow-band pixel locations, further comprising:
(i) recording a set of recorded shifts in the pixel locations as the wideband pseudo-projections are aligned spatially; and
(j) applying the recorded shifts to the narrow-band pixel locations, thereby bringing them into spatial alignment.

11. The method of claim 1 wherein the images are pseudo-projections.

12. The method of claim 1 wherein a sequence of images is acquired using wideband light to provide a spatial reference for the narrow-band images.

13. The method of claim 1 wherein the set of wavelength bands is selected from the group consisting of wideband and overlapping wavelengths and narrow-band and non-overlapping wavelengths.

14. The method of claim 1 wherein the set of wavelength bands comprises at least two wideband spectral regions.

15. The method of claim 1 wherein the plurality of cross-sectional images comprise a plurality of narrow-band images and at least one wideband image collected using a wide band of wavelengths, where said wideband image provides a reference for motion-correcting the narrow-band images.

16. The method of claim 1 wherein the biological object comprises at least one labeling molecule.

17. A method for 3D imaging of a biologic object in an optical tomography system comprising:
(a) operating an optical tomography system with a processor, where the optical tomography system includes a microscope having an objective lens, a computer-controlled light source and a condenser lens assembly aligned along an optical axis, the optical tomography system also including a photodetector array for receiving light transmitted through the objective lens;
(b) labeling a subcellular structure of the biological object by introducing at least one nanoparticle-biomarker;
(c) positioning the labeled biological object relatively to a microscope objective to present varying angles of view;
(d) illuminating the labeled biological object with radiation having wavelengths between 150 nm and 900 nm so that the at least one nanoparticle-biomarker is selected to emit or absorb radiation having wavelengths between 150 and 900 nm;
(e) filtering a portion of the produced radiation using a set of filters to produce filtered signals within a set of wavelength bands;
(f) sensing the filtered signals transmitted through the labeled biological object and the microscope objective within the set of wavelength bands to produce image data;
(g) repeating steps (c) through (f) until a set of image data from varying angles of view has been produced;
(h) forming a set of pseudo-projections of the biological object from the set of image data;
(i) reconstructing the plurality of cross-sectional images to form a 3D image of the labeled biological object;
(j) computing a mass for each of the set of pseudo-projections to generate a set of pseudo-projection mass values;
(k) normalizing the set of pseudo-projection mass values to a common reference to produce a normalized set of pseudo-projection mass values; and
(l) generating a 3D image reconstruction of the object corrected by the normalized set of pseudo-projection mass values.

18. The method of claim 17 where normalizing the set of pseudo-projection mass values comprises dividing each pixel intensity in the set of pseudo-projections by a normalization value factor so that the sum of the pixels in each normalized pseudo-projection adds up to the common reference value.

19. The method of claim 17 further comprising:
measuring an illumination gradient; applying illumination gradient corrections to each pseudo-projection to generate a set of corrected pseudo-projections; and
using the set of corrected pseudo-projections to generate the set of pseudo-projection mass values.

20. The method of claim 19 where the set of corrected pseudo-projections comprise values computed according to a formula:

$$I\_ij \rightarrow I\_ij * sum(I\_ref)/(sum(I\_ij))$$

where I_ij is the intensity of a single pixel;
sum(I_ij) is the sum of all the intensities of all the pixels (for i=1 to imax, j=1 to jmax); and
I_ref is a reference image or set of values.

21. A system for 3D imaging of cells in an optical tomography system comprising:
- at least one labeled biological object of interest;
- a delivery device positioned in an optical path relative to a microscope objective;
- at least one illumination source for producing light having a spectral bandwidth with wavelengths between 150 and 900 nm, wherein the illumination source employs plasmon resonance energy transfer (PRET), wherein the employment of PRET comprises:
  - (a) using a dark-field microscopy configuration, wherein light scattered at high angles relative to the incident light is collected by the objective lens; and
  - (b) incorporating into the labeled biological object at least one ensemble of metallic nanoparticles, each ensemble of metallic nanoparticles having at least one substantially identical labeling molecule attached to the surface of substantially each nanoparticle that is a member of the at least one ensemble of metallic nanoparticles;
- an objective lens being located to receive the light emanating from a labeled region of interest from a biological object;
- an axial translation mechanism coupled to translate the objective lens through a scanning range so as to extend the depth of field;
- a rotating mechanism for turning the object of interest to present a plurality of different views to the objective lens;
- a set of chromatic filters for selectively inserting into at least one optical path, wherein the set of filters produce filtered signals within a set of wavelength bands;
- at least one camera positioned to receive at least one wavelength of the light radiation emanating from the labeled biological object and the microscope objective;
- an image processor coupled to receive data from the at least one camera, where the image processor generates image data; and
- a reconstruction module coupled to the image processor, where the reconstruction module processes the image data to form a 3D image of the cell.

22. The system of claim 21 further comprising means for distinguishing radiation composed of wavelengths contained within at least one separate spectral band.

23. The system of claim 21 further comprising means for inserting at least two biomarkers into the object of interest.

24. The system of claim 21 further comprising means for motion-correcting the image information acquired from at least two wavelength bands.

25. The system of claim 24 wherein the means for motion-correcting the image information acquired from at least two wavelength bands comprises means for acquiring image information for a wide spectral band.

26. The system of claim 21 wherein the cross-sectional images comprise pseudo-projections.

27. The system of claim 21 wherein the at least one camera is selected from the group consisting of a monochrome camera, a wideband camera and a color camera.

28. The system of claim 21 wherein the at least one camera comprises at least four monochrome cameras.

29. The system of claim 21 wherein the at least one camera comprises a color camera and a wideband camera.

30. The system of claim 29 wherein the set of filters is replaced by a multi-bandpass filter.

* * * * *